United States Patent [19]

Ravichandran et al.

[11] Patent Number: 5,021,478

[45] Date of Patent: Jun. 4, 1991

[54] COMPOUNDS CONTAINING BOTH UV-ABSORBER AND 1-HYDROCARBYLOXY HINDERED AMINE MOIETIES AND STABILIZED COMPOSITIONS

[75] Inventors: Ramanathan Ravichandran, Nanuet; James P. Galbo, Hartsdale, both of N.Y.

[73] Assignee: Ciba-Geigy Corporation, Ardsley, N.Y.

[21] Appl. No.: 479,880

[22] Filed: Feb. 14, 1990

Related U.S. Application Data

[63] Continuation-in-part of Ser. No. 326,848, Mar. 21, 1989, abandoned.

[51] Int. Cl.[5] .................. C08K 5/3435; C08K 5/3492; C07D 211/34; C07D 403/00
[52] U.S. Cl. ........................................ 524/91; 524/99; 524/100; 524/102; 524/103; 544/183; 544/194; 544/219; 546/222; 546/223; 546/224
[58] Field of Search .................. 524/91, 99, 100, 102, 524/103; 544/183, 194, 219; 546/222, 223, 224, 182

[56] References Cited

U.S. PATENT DOCUMENTS

| | | | |
|---|---|---|---|
| 4,314,933 | 2/1982 | Berner | 524/91 |
| 4,344,876 | 8/1982 | Berner | 524/91 |
| 4,426,471 | 1/1984 | Berner | 524/91 |
| 4,426,472 | 1/1984 | Berner | 524/99 |
| 4,619,956 | 10/1986 | Susi | 524/87 |
| 4,665,185 | 5/1987 | Winter et al. | 546/184 |

OTHER PUBLICATIONS

Shlyapintokh et al., "Developments in Polymer Stabilisation", V 41–70. (1982).

Primary Examiner—Kriellion Morgan
Attorney, Agent, or Firm—Luther A. R. Hall

[57] ABSTRACT

Compounds containing both a UV-absorbing moiety and a 1-hydrocarbyloxy hindered amine moiety are effective stabilizers for protecting polymer compositions against the deleterious effects of actinic light. The UV-absorbing moieties include the substituted 2H-benzotriazoles, s-triazines, acrylates, benzophenones, oxanilides and oxamides.

35 Claims, No Drawings

COMPOUNDS CONTAINING BOTH UV-ABSORBER AND 1-HYDROCARBYLOXY HINDERED AMINE MOIETIES AND STABILIZED COMPOSITIONS

This is a continuation-in-part of application Ser. No. 326,848, filed on Mar. 21, 1989, now abandoned.

Compounds containing both a UV-absorbing and a 1-hydrocarbyloxy hindered amine moieties are very effective stabilizers for protecting polymers from the deleterious effects of actinic light.

BACKGROUND OF THE INVENTION

It is known in the art that the concomitant use of a hindered amine light stabilizer with a UV-absorber such as a 2H-benzotriazole provides excellent stabilization in many polymer compositions as summarized by G. Berner and M. Rembold, "New Light Stabilizers for High-Solids Coatings", Organic Coatings Science and Technology, Vol 6, Dekkar, New York, 1984, pp 55-85.

Molecules containing both a UV-absorber moiety and a hindered amine moiety with an N-H, N-alkyl or N-alkanoyl group are described in U.S. Pat. Nos. 4,344,876; 4,426,471; 4,314,933; and 4,619,956; British Patent Application 2,188,631; and L. Awar, et al, "New Anti-UV Stablizers for Automotive Coatings" (Presented at 1988 Annual Meeting of Federation of Societies for Coatings Technology).

The concomitant use of a separate hindered amine molecule and a separate UV-absorber molecule is also taught in U.S. Pat. No. 4,619,956.

N-Hydrocarbyloxy derivatives of hindered amine light stabilizers are less basic than the corresponding N-H or N-alkyl derivatives. As such, the N-hydrocarbyloxy derivatives offer an important advantage in polymer systems where the basicity of hindered amines generally causes undesired interactions with the polymer system such as cure retardation in high solids thermoset acrylic automotive coatings.

The instant N-hydrocarbyloxy derivatives being less basic do not cause cure retardation in such polymer systems.

OBJECTS OF THE INVENTION

One object of the instant invention is to provide novel compounds which have present in the same molecule a UV-absorbing moiety and an N-hydrocarbyloxy hindered amine moiety.

Another object of the instant invention is to provide polymer compositions stabilized against the deleterious effects of actinic light by the presence of an effective amount of a novel compound described supra.

DETAILED DISCLOSURE

The instant invention pertains to a compound having one of the formulas I to VI

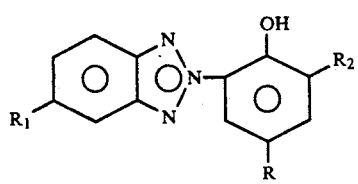

(I)

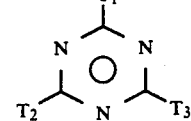

(II)

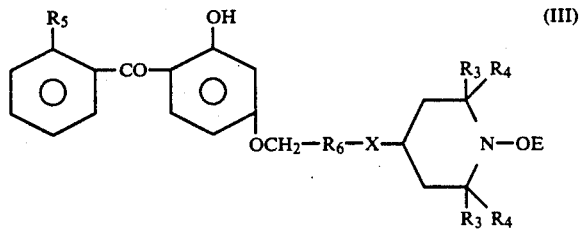

(III)

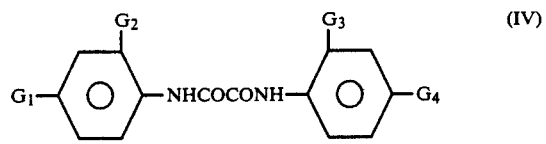

(IV)

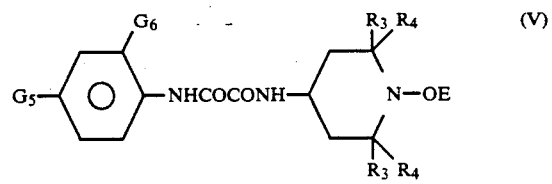

(V)

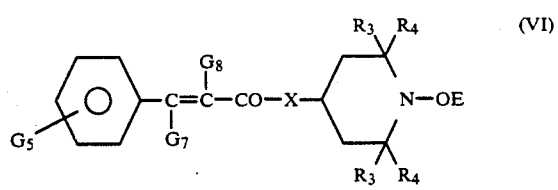

(VI)

wherein $R_1$ is hydrogen, halogen, alkyl of 1 to 12 carbon atoms or aralkyl of 7 to 15 carbon atoms, R and $R_2$ are independently hydrogen, alkyl of 1 to 12 carbon atoms, aralkyl of 7 to 15 carbon atoms or the group of formula VII

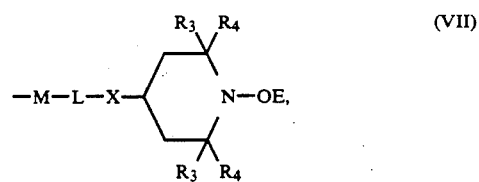

(VII)

with the proviso that one of R and $R_2$ is a group of formula VII, $R_3$ and $R_4$ are independently alkyl of 1 to 4 carbon atoms or together $R_3$ and $R_4$ are pentamethylene, M is a direct bond, $-NG_9-$, $-O-$, $-S-$, $-SO_2NG_9$, $-SO_2-$, $-SO_2O-$, $-CONG_9-$, $-COO-$ or $-OCO-$, L is a direct bond, alkylene of 1 to 12 carbon atoms, alkenylene of 3 to 18 carbon atoms, alkynylene of 3 to 18 carbon atoms, cycloalkylene of 5 to 12 carbon atoms, said alkylene interrupted by one or more $-O-$ atoms, X is $-COO-$, $-CONG_9-$, $-O-$, $-NG_9-$ or $-NY-$ where $G_9$ is hydrogen or alkyl of 1 to 8 carbon atoms, $R_5$ is hydrogen or hydroxyl, $R_6$ is —CO—, —CHOHCH$_2$— or —CH(CH$_2$OH)—, $G_1$, $G_2$, $G_3$ and $G_4$ are independently hydrogen, halogen, alkyl of 1 to 12 carbon atoms, aryl of 6 to 10 carbon atoms, aralkyl of 7 to 15 carbon atoms, phenoxy, alkoxy of 1 to 12 carbon atoms, —OCH$_2$COO—L$_1$ or the group T
where
$L_1$ is alkyl of 1 to 8 carbon atoms, and
T is

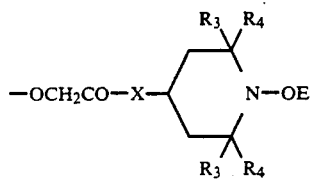

with the proviso that at least one of $G_1$ to $G_4$ must be T, $G_5$ and $G_6$ have independently the same definitions as $G_1$ to $G_4$, with the proviso that at least one of $G_5$ and $G_6$ do not need to be T, $G_7$ is hydrogen, phenyl or phenyl substituted by $G_5$, $G_8$ is cyano, —COO—L$_1$ or —CO—X—Y, where

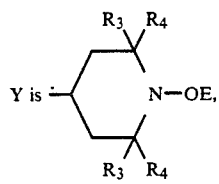

E is hydrogen, alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, $T_1$, $T_2$ and $T_3$ are independently alkyl of 1 to 12 carbon atoms, aryl of 6 to 10 carbon atoms, said aryl substituted by one or two alkyl of 1 to 4 carbon atoms, aralkyl of 7 to 15 carbon atoms, —OR$_7$, —SR$_7$, —NR$_7$R$_8$, —SO$_3$H, or o-hydroxyphenyl substituted by the group T, with the proviso that at least one of $T_1$, $T_2$ and $T_3$ must be o-hydroxyphenyl substituted by the group T, and $R_7$ and $R_8$ are independently hydrogen, alkyl of 1 to 18 carbon atoms, alkenyl of 2 to 18 carbon atoms, alkoxyalkyl of 2 to 12 carbon atoms, cycloalkyl of 5 to 12 carbon atoms, aryl of 6 to 10 carbon atoms, said aryl substituted by one or two alkyl of 1 to 4 carbon atoms, aralkyl of 7 to 15 carbon atoms, or the group Y.

Preferably $R_1$ is hydrogen, chloro, alkyl of 1 to 4 carbon atoms or alpha,alpha-dimethylbenzyl; most preferably hydrogen or chloro.

$R_2$ is preferably alkyl of 1 to 8 carbon atoms or alpha,alpha-dimethylbenzyl; most preferably methyl, tert-butyl, tert-amyl or tert-octyl.

Preferably R is a group of formula VII where M is a direct bond, L is ethylene and X is —COO—.

$R_3$ and $R_4$ are preferably both methyl.

$R_5$ is preferably hydrogen.

$R_6$ is preferably —CO—.

$G_1$ and $G_4$ are preferably each hydrogen,

Preferably $G_5$ is hydrogen.

$G_3$ or $G_6$ is preferably the group T, ethoxy or —OCH$_2$COO—L$_1$ where L$_1$ is alkyl of 2 to 8 carbon atoms; most preferably L$_1$ is ethyl, n-butyl, n-octyl or isooctyl.

$G_7$ is preferably hydrogen.

$G_8$ is preferably cyano.

Preferably X is —O— or —NH—.

E is preferably alkyl of 1 to 12 carbon atoms, cyclohexyl or alpha-methylbenzyl; most preferably methyl, heptyl, octyl, nonyl, cyclohexyl or alpha-methylbenzyl.

SYNTHESIS

The instant compounds are prepared by the general methods set forth in prior art references cited supra for preparing the N-unsubstituted or N-alkyl substituted compounds containing both UV-absorber and hindered amine moieties.

1-Hydrocarbyloxy hindered amines are prepared by the methods set forth in copending patent applications Ser. Nos. 259,950 now abandoned and 259,949 now abandoned.

The intermediates used to make the instant compounds are largely items of commerce.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

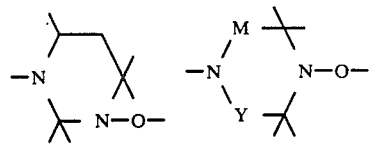

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/ isobutylene, ethylene/butene-1, propylene/butadiene, isobutylene/isoprene, ethylene/alkyl acrylates, ethylene/ alkyl methacrylates, ethylene/vinyl acetate or ethylene/ acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/ propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/ vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-pbenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone -acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants

1.1. Alkylated Monophenols, for Example 2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert-butyl-4-methoxymethylphenol

1.2. Alkylated Hydroquinones, for Example 2,6-di-tert-butyl-4-methoxyphenol
2,5-di-tert-butyl-hydroquinone
2,5-di-tert-amyl-hydroquinone
2,6-diphenyl-4-octadecyloxyphenol

1.3. Hydroxylated Thiodiphenyl Ethers, for Example 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-Bisphenols, for Example 2,2'-methylene-bis-(6-tert-butyl-4-methylphenol)
2,2'-methylene-bis-(6-tert-butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalat

1.5. Benzyl Compounds, for Example 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt

1.6. Acylaminophenols, for Example 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate

1.7. Esters of $\beta$-(3,5-di-tert-butyl-4-hydroxyphenyl)-propionic Acid with Monohydric or Polyhydric Alcohols, for Example

| methanol | diethylene glycol |
|---|---|
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of $\beta$-(5-tert-butyl-4-hydroxy-3-methylphenyl)-Propionic Acid with Monohydric or Polyhydric Alcohols, for Example

| methanol | diethylene glycol |
|---|---|
| octadecanol | triethylene glycol |
| 1,6-hexanediol | pentaerythritol |

| | |
|---|---|
| neopentyl glycol | tris-hydroxyethyl isocyanurate |
| thiodiethylene glycol | di-hydroxyethyl oxalic acid diamide |

1 9. Amides of
β-(3,5-di-tert-butyl-4-hydroxyphenyl)-Propionic Acid
for Example

N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine

2. UV Absorbers and Light Stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tertbutyl-, 5-chloro-3'-tert-butyl-5'-methyl-, 3'-sec-butyl-, 5'-tert-butyl-, 4'-octoxy, 3',5'-di-tert-amyl-, 3',5'-bis(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tertbutylbenzoyl)-resorcinol, benzoylresorcinol, 3,5-di-tertbutyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris (2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-dodecyloxy-5,5'-di-tertbutyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o-and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy(phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy 4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tertbutylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/ melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are referenced in a paper by H. J. Heller in European Polymer Journal Supplement, 1969, pp. 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tertbutyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-$\beta,\beta$-diphenylacrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alphacarbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl) -4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tertamylphenyl)-2H-benzotriazole, 2-[2-hydroxy-3-tert-butyl-5 -(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl) ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alphadimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising
(a) an acid catalyzed thermoset coating or enamel based on hot crosslinkable acrylic, polyester or alkyd resins,
(b) a NOE-substituted 2,2,6,6-tetralkylpiperidine compound, and
(c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1

1-Methoxy-2,2,6,6-tetramethylpiperidin-4-yl 3-(2H-Benzotriazol-2-yl)-5-tert-butyl-4-hydroxyhydrocinnamate A mixture of 30.0 grams (84.9 mmol) of methyl 3-(2H-benzotriazol-2-yl)-5-tert-butyl-4-hydroxyhydrocinnamate, 19.1 grams (102 mmol) of 4-hydroxy-1-methoxy-2,2,6,6-tetramethylpiperidine, and 200 ml of xylene is heated at reflux in a round-bottomed flask equipped with a fractionating column and an adjustable still head. Approximately 25 ml of wet xylene is distilled from the reaction mixture. The reaction mixture is then cooled to 100° C., treated with 1.4 gram of lithium amide, and diluted with 100 ml of xylene. The mixture is heated at reflux for sixteen hours while methanol is removed by fractional distillation. The reaction mixture is diluted with 200 ml of toluene, and washed successively with 1N hydrochloric acid (200 ml) and saturated sodium bicarbonate solution (300 ml). Solids are removed by filtration, and the filtrate is dried over anhydrous magnesium sulfate and then concentrated to obtain a brown solid. The crude product is passed through a layer of silica gel (2:1 heptane:ethyl acetate). The eluent is evaporated to give a solid which is recrystallized from isopropanol to afford 24.5 grams (57% yield) of the title compound as a white solid melting at 135°–137° C.

Analysis:
Calcd for $C_{29}H_{40}N_4O_4$: C, 68.5; H, 7.9; N, 11.0.
Found: C, 68.3; H, 8.3; N, 10.8.

EXAMPLE 2

1-Cyclohexyloxy-2,2,6,6-tetramethylpiperidin-4-yl 3-(2H-Benzotriazol-2-yl)-5-tert-butyl-4-hydroxyhydrocinnamate The title compound is a white solid melting at 138°–140° C. which is prepared according to the procedure of Example 1 by substituting an equivalent amount of 1-cyclohexyloxy-4-hydroxy-2,2,6,6-tetramethylpiperidine for 4-hydroxy-1-methoxy-2,2,6,6-tetramethylpiperidine.

Analysis:
Calcd for $C_{34}H_{48}N_4O_4$: C, 70.8; H, 8.4; N, 9.7.
Found: C, 70.9; H, 8.4; N, 9.8.

EXAMPLE 3

1-Octyloxy-2,2,6,6-tetramethylpiperidin-4-yl 3-(2H-Benzotriazol-2-yl)-5-tert-butyl-4-hydroxyhydrocinnamate The title compound is a yellow syrup which is prepared by the procedure according to Example 1 by substituting an equivalent amount of 4-hydroxy-1-octyloxy-2,2,6,6-tetramethylpiperidine for 4-hydroxy-1-methoxy-2,2,6,6-tetramethylpiperidine.

Analysis:
Calcd for $C_{36}H_{54}N_4O_4$: C, 71.3; H, 9.0; N, 9.2.
Found: C, 71.5; H, 8.8; N, 9.2.

EXAMPLE 4

N-(1-Octyloxy-2,2,6,6-tetramethylpiperidin-4-yl) -3-(2H-benzotriazol-2-yl)-5-tert-butyl-4-hydroxyhydrocinnamamide A mixture of 4.0 g (11.3 mmol) of methyl 3-(2H-benzotriazol-2-yl)-5-tert-butyl-4-hydroxyhydrocinnamate and 8.0 g (28.1 mmol) of 4-amino-1-octyloxy-2,2,6,6-tetramethylpiperidine is heated at 190°–200° C. for 2 hours. The reaction mixture is dissolved in ethyl acetate (300 ml). The organic solution is washed with 1N hydrochloric acid (2 ×100 ml) and saturated sodium bicarbonate solution (200 ml), then dried over magnesium sulfate and evaporated to obtain a solid. Purification by flash chromatography on silica gel (3:1 heptane: ethyl acetate) following by recrystallization from methanol affords 1.0 g (15% yield) of the title compound, a white solid, mp 153°–9° C.

Anal. Calcd. for $C_{36}H_{55}N_5O_3$: C, 71.4; H, 9.1; N, 11.6.
Found: C, 71.4; H, 9.4; N, 11.5.

EXAMPLE 5A

Methyl 4-Benzoyl-3-hydroxyphenoxyacetate

A mixture of 15.0 g (70.0 mmol) of 2,4-dihydroxybenzophenone, 10.7 g (70 mmol) of methyl bromoacetate, 19.3 g (0.14 mol) of potassium carbonate, and 125 ml of N,N-dimethylformamide is stirred at 25° C. for 18 hours. The reaction mixture is partitioned between diethyl ether and 0.5 N hydrochloric acid. Solids are removed by filtration, and the filtrate is dried over magnesium sulfate and concentrated. The concentrate is partially dissolved in diethyl ether, and solids are removed by filtration. The solid material is recrystallized from dichloromethane: 2-propanol to afford 13.7 g (69% yield) of the title compound, a pale yellow solid, mp 131°–4° C.

EXAMPLE 5B

2-Hydroxy-4-[(1-octyloxy-2,2,6,6-tetramethylpiperidin-4-yloxy)-carbonylmethoxy]benzophenone A mixture of 22.0 g (76.8 mmol) of methyl 4-benzoyl-3-hydroxyphenoxyacetate, 32.9 g (0.115 mol) of 4-hydroxy-1-octyloxy-2,2,6,6-tetramethylpiperidine, and 100 ml of xylene is heated at reflux. Water is removed by fractional distillation. The reaction mixture is cooled to 80° C., treated with 2.1 g of lithium amide, and diluted with 50 ml of xylene. The reaction mixture is heated at reflux for 2 hours, and methanol is removed by fractional distillation. The reaction mixture is cooled, then diluted with diethyl ether (250 ml). The organic solution is washed with 1N hydrochloric acid (200 ml), and solids are removed by filtration. The solution is washed with saturated sodium bicarbonate solution (100 ml), dried over magnesium sulfate, and concentrated to an oil. Purification by flash chromatography on silica gel (85:15 heptane: ethyl acetate) affords 32.6 g (79% yield) of the title compound, a yellow syrup.

Anal. Calcd. for $C_{32}H_{45}NO_6$: C, 71.2; H, 8.4; N, 2.6.
Found: C, 71.6; H, 8.7; N, 2.6.

EXAMPLE 6

2-Hydroxy-4-[(1-cyclohexyloxy-2,2,6,6-tetramethylpiperidin-4-yl) -aminocarbonylmethoxy]benzophenone The title compound is prepared by the reaction of 2,4-dihydroxybenzophenone with potassium carbonate and ethyl chloroacetate followed by reaction with 4-amino-1-cyclohexyloxy-2,2,6,6-tetramethylpiperidine.

EXAMPLE 7

2-Hydroxy-4-[3-(1-methoxy-2,2,6,6-tetramethylpiperidin-4-yloxy) -2-hydroxypropoxy]benzophenone The title compound is prepared by reaction of 2,4-dihydroxybenzophenone with epichlorohydrin followed by reaction with 4-hydroxy-1-methoxy-2,2,6,6-tetramethylpiperidine.

EXAMPLE 8A 2,4-Bis(2,4-dimethylphenyl)-6-(2,4-dihydroxyphenyl)-s-triazine

The title compound is prepared by the reaction of cyanuric chloride with m-xylene followed by reaction with resorcinol. Aluminum chloride is used as a reagent in both reactions.

EXAMPLE 8B 2,4-Bis(2,4-dimethylphenyl)-6-[2-hydroxy-4-((1-octyloxy-2,2,6,6-tetramethylpiperidin-4-yloxy)carbonylmethoxy)-phenyl]-s-triazine A solution of 14.5 g (40.0 mmol) of 1-octyloxy-2,2,6,6-tetramethylpiperidin-4-yl chloroacetate in 25 ml of N,N-dimethylformamide is rapidly added to a mixture of 20.0 g (50.2 mmol) of 2,4-bis(2,4-dimethylphenyl)-6-(2,4-dihydroxyphenyl)-1,3,5-triazine (Example 8A), 125 ml of N,N-dimethylformamide, and 4.0 g of 50% sodium hydroxide solution that has been stirred at ambient temperature for 30 minutes. The reaction mixture is then heated at 70° C. for 1 hour and stirred at ambient temperature for 17 hours. The reaction mixture is partitioned between ethyl acetate (300 ml) and a mixture of water (1000 ml) and 1N hydrochloric acid (10 ml). The aqueous layer is extracted with diethyl ($2 \times 500$ ml) and saturated sodium chloride solution (500 ml), dried over magnesium sulfate, and concentrated to an oil. Purification by flash chromatography on silica gel (5:1 heptane: ethyl acetate) affords 14.0 g (48% yield) of the title compound, a yellow solid, mp 86°–90° C.

Anal. Calcd. for $C_{44}H_{58}N_4O_5$: C, 73.1; H, 8.1; N, 7.7. Found: C, 72.8; H, 8.1; N, 7.6.

EXAMPLE 9

2,4-Bis(2,4-dimethylphenyl)-6-[2-hydroxy-4-(N-(1-cyclohexyloxy-2,2,6,6-tetramethylpiperidin-4-yl)aminocarbonylmethoxy)phenyl]-s-triazine The title compound is prepared according to the procedure of Example 8 by substituting 4-amino-1-cyclohexyloxy-2,2,6,6-tetramethylpiperidine for an equivalent amount of 4-hydroxy-1-octyloxy-2,2,6,6-tetramethylpiperidine.

EXAMPLE 10A

2-Ethoxy-2'-[(ethoxycarbonyl)methoxy]oxanilide

The title compound is prepared by the reaction of 2,2'-di-hydroxyoxanilide with two equivalents of potassium carbonate, one equivalent of ethyl bromide and one equivalent of ethyl chloroacetate.

EXAMPLE 10B

2-Ethoxy-2'-[(1-octyloxy-2,2,6,6-tetramethylpiperidin-4-yloxy)-carbonylmethoxy]oxanilide The title compound is prepared by reacting the compound prepared in Example 10A with 4-hydroxy-1-octyloxy-2,2,6,6-tetramethylpiperidine and a catalytic amount of lithium amide.

EXAMPLE 11

2-Ethoxy-2'-[N-(1-cyclohexyloxy-2,2,6,6-tetramethylpiperidin-4-yl) aminocarbonylmethoxy]oxanilide A solution of 3.5 g (10.7 mmol) of N-(1-cyclohexyloxy-2,2,6,6-tetramethylpiperidin-4-yl)-2-chloroacetamide in 20 ml of N,N-dimethylformamide is added over a 5 minute period to a mixture of 3.2 g (10.7 mmol) of 2-ethoxy-2'-hydroxyoxanilide, 0.9 g of 50% sodium hydroxide solution, and 25 ml of N,N-dimethylformamide that has been heated to 60° C. The reaction mixture is then heated at 60° C. for one hour and at 90° C. for another hour. The reaction mixture is quenched with 500 ml of water. The crude solid is isolated and washed with water, then dissolved in dichloromethane (150 ml). The organic solution is dried over magnesium sulfate and concentrated to a volume of 40 ml. Methanol (100 ml) is added to precipitate the product, which is isolated by filtration to afford 4.9 g (77% yield) of the title compound, a white crystalline material, mp 190°–192° C.

Anal. Calcd. for $C_{33}H_{46}N_4O_6$: C, 66.6; H, 7.8; N, 9.4. Found: C, 66.3; H, 7.7; N, 9.2.

EXAMPLE 12

2,2'-Bis[N-(1-octyloxy-2,2,6,6-tetramethylpiperidin-4-yl) -aminocarbonylmethoxy]oxanilide The title compound is prepared by the reaction of 2,2'dihydroxyoxanilide with two equivalents of each of potassium carbonate and ethyl chloroacetate, followed by reaction with two equivalents of 4-amino-1-octyloxy-2,2,6,6-tetramethylpiperidine.

EXAMPLE 13A

N-(2-Hydroxyphenyl)-N'-(1-octyloxy-2,2,6,6-tetramethylpiperidin-4-yl)oxamide

The title compound is prepared by the reaction of diethyl oxalate with one equivalent each of 2-hydroxyaniline and of 4-amino-1-octyloxy-2,2,6,6-tetramethylpiperidine.

EXAMPLE 13B

N-(2-Ethoxyphenyl)-N'-(1-octyloxy-2,2,6,6-tetramethylpiperidin-4-yl)oxamide

The above-named compound is prepared by reacting the compound prepared in Example 13A with potassium carbonate and ethyl bromide.

EXAMPLE 14

N-[2-((1-Octyloxy-2,2,6,6-tetramethylpiperidin-4-yloxy) -carbonylmethoxy)phenyl]-N'-(1-octyloxy-2,2,6,6-tetramethylpiperidin-4-yl)oxamide The compound prepared in Example 13A is reacted with potassium carbonate and ethyl chloroacetate, and then reacted with 4-hydroxy-1-octyloxy-2,2,6,6-tetramethylpiperidine and a catalytic amount of lithium amide to form the title compound.

EXAMPLE 15

N-[2-(N-(1-Octyloxy-2,2,6,6-tetramethylpiperidin-4-yl) aminocarbonylmethoxy)phenyl]-N'-(1-octyloxy-2,2,6,6-tetramethylpiperidin-4-yl)oxamide The title compound is prepared according to the procedure of Example 14 by substituting an equivalent amount of 4-amino-1-octyloxy-2,2,6,6-tetramethylpiperidine for 4-hydroxy-1-octyloxy-2,2,6,6-tetramethylpiperidine.

EXAMPLE 16A

N-Butyl-N-(1-methoxy-2,2,6,6-tetramethylpiperidin-4-yl)-chloroacetamide

A solution of 48.5 g (0.200 mol) of 4-butylamino-1-methoxy-2,2,6,6-tetramethylpiperidine in 150 ml of dichloromethane is added over a one hour interval at $-10°$ C. to a solution of 11.3 g (0.100 mol) of chloroacetyl chloride in 100 ml of dichloromethane. The reaction mixture is then stirred at ambient temperature for 1 hour. The mixture is diluted with diethyl ether (500 ml), and solids are removed by filtration. The filtrate is washed with 1N hydrochloric acid (2×75 ml) and saturated sodium bicarbonate (100 ml), then dried over magnesium sulfate and concentrated to afford 27.8 g (87% yield) of the title compound, a pale yellow oil.

EXAMPLE 16B

2-Hydroxy-4-[N-(1-methoxy-2,2,6,6-tetramethylpiperidin-4-yl)
-N-butylaminocarbonylmethoxy]benzophenone A mixture of 10.1 g (47.0 mmol) of 2,4-dihydroxybenzophenone, 15.0 g (47.0 mmol) of N-butyl-N-(1-methoxy-2,2,6,6-tetramethylpiperidin-4-yl)chloroacetamide, 19.5 g (0.141 mol) of potassium carbonate, 0.8 g (4.7 mmol) of potassium iodide, and 100 ml of N,N-dimethylformamide is heated at 80° C. for 20 hours. The reaction mixture is treated with 1N hydrochloric acid (600 ml). The brown precipitate is dissolved in ethyl acetate (400 ml), and this solution is washed with water (200 ml) and saturated sodium chloride solution (200 ml), then dried over magnesium sulfate and concentrated to a glass. Purification by flash chromatography on silica gel (3:1 heptane: ethyl acetate) affords 5.4 g (23% yield) of the title compound, a yellow glass.

Anal. Calcd. for $C_{29}H_{40}N_2O_5$: C, 70.1; H, 8.1; N, 5.6. 1066

Found: C, 70.4; H, 8.4; N, 5.3.

EXAMPLE 17A

1-Cyclohexyloxy-2,2,6,6-tetramethylpiperidin-4-yl Chloroacetate

A mixture of 45.2 g (0.177 mol) of 1-cyclohexyloxy-4-hydroxy-2,2,6,6-tetramethylpiperidine, 17.9 g (0.177 mol) of triethylamine, and 150 ml of dichloromethane is added over a 1 hour interval at 5° C. to a solution of 20.0 g (0.177 mol) of chloroacetyl chloride in 100 ml of dichloromethane. The reaction mixture is stirred at ambient temperature for 1 hour and then diluted with diethyl ether (500 ml). Solids are removed by filtration, and the filtrate is washed with 1N hydrochloric acid (2×100 ml), saturated sodium bicarbonate solution (200 ml), and saturated sodium chloride solution (200 ml), then dried over magnesium sulfate and concentrated to obtain an oil. Purification by flash chromatography on silica gel (5:1 heptane: ethyl acetate) affords 22.6 g (39% yield) of the title compound, a white solid, mp 62°-4° C.

EXAMPLE 17B

2-[(1-Cyclohexyloxy-2,2,6,6-tetramethylpiperidin-4-yloxy) -carbonylmethoxy]-2'-hydroxyoxanilide A solution of 8.7 g (26.2 mmol) of 1-cyclohexyloxy-2,2,6,6-tetramethylpiperidine-4-yl chloroacetate in 55 ml of N,N-dimethylformamide is added over a 5 min. interval to a mixture of 14.3 g (52.4 mmol) of 2,2'-dihydroxyoxanilide, 1.1 g (27.5 mmol) of sodium hydroxide, and 80 ml of N,N-dimethylformamide. The reaction mixture is heated at 60° C. for 2 hours, then partitioned between ethyl acetate (300 ml) and water (500 ml). The organic phase is dried over magnesium sulfate and concentrated to an oil which is triturated with 2:1 heptane: ethyl acetate to precipitate unreacted 2,2'-dihydroxyoxanilide. The organic solution is concentrated and purified by flash chromatography on silica gel (2:1 heptane: ethyl acetate) to afford 6.2 g 942% yield) of the title compound, a white solid, mp 180°-82° C.

Anal. Calcd. for $C_{31}H_{41}N_3O_7$: C, 65.6; H, 7.3; N, 7.4.
Found: C, 65.5; H, 7.4; N, 7.3.

EXAMPLE 17C

2'-Ethoxy-2-[(1-cyclohexyloxy-2,2,6,6-tetramethyl-piperidin -4-yloxy)-carbonylmethyl]oxanilide A solution of 1.6 g (10.2 mmol) of ethyl iodide in 10 ml of N,N-dimethylformamide is added rapidly to a mixture of 5.8 g (10.2 mmol) of 2-[(1-cyclohexyloxy-2,2,6,6-tetramethylpiperidin-4-yloxy) -carbonylmethoxy]-2'-hydroxyoxanilde, 0.41 g (10.2 mmol) of sodium hydroxide, and 50 ml of N,N-dimethylformamide. The reaction mixture is heated at 60° C. for 2 hours, and then treated with 0.3 g (1.9 mmol) of ethyl iodide and 0.1 g (2.5 mmol) of sodium hydroxide. The mixture is heated at 60° C. for another hour and poured onto crushed ice. The resulting precipitate is collected by filtration, washed with water, and dissolved in dichloromethane (100 ml). The organic solution is dried over magnesium sulfate and evaporated to obtain an oil. Crystallization from 2-propanol affords 4.6 g (75% yield) of the title compound, a white solid, mp 128°-30° C.

Anal. Calcd. for $C_{33}H_{45}N_3O_7$: C, 66.5; H, 7.6; N, 7.1.
Found: C, 66.4; H, 7.7; N, 6.9.

EXAMPLE 18

2,2'-Bis-[(1-cyclohexyloxy-2,2,6,6-tetramethylpiperidin-4-yloxy)-carbonylmethoxy]oxanilide A solution of 13.0 g (39.2 mmol) of 1-cyclohexyloxy-2,2,6,6-tetramethylpiperidin-4-yl chloroacetate (Example 17A) in 50 ml of N,N-dimethylformamide is added over 5 minutes to a mixture of 5.33 g (19.6 mmol) of 2,2'-dihydroxyoxanilide, 1.57 g (39.2 mmol) of sodium hydroxide, and 75 ml of N,N-dimethylformamide. The reaction temperature reaches 36° C. during the addition. The reaction mixture is heated at 60° C. for 1 hour and diluted with water (700 ml). Solids are collected by filtration and washed with water, then dissolved in dichloromethane (300 ml). The organic solution is dried over magnesium sulfate, concentrated to a volume of approximately 100 ml, and diluted with warm 2-propanol (200 ml) to induce crystallization. The yield of the title compound, a white solid, mp 201°-202° C., is 14.0 g (83% yield).

Anal. Calcd. for $C_{48}H_{70}N_4O_{10}$: C, 66.8; H, 8.2; N, 6.5.
Found: C, 67.4; H, 9.5; N, 6.6.

EXAMPLE 19

N-(2-Octyloxycarbonylmethoxyphenyl)-N'-(1-octyloxy-2,2,6,6-tetramethylpiperidin-4-yl)oxamide A two-phase mixture of 12.5 g (97.0 mmol) of 70% aqueous tert-butyl hydroperoxide, 75 ml of octane, and 0.5 g of sodium chloride is agitated in a separatory funnel. The organic phase is dried over magnesium sulfate and diluted with 25 ml of octane. A mixture of 9.5 g 919.4 mmol) of N-(2-octyloxycarbonylmethoxyphenyl)-N'-(2,2,6,6-tetramethylpiperidin-4-yl)oxamide, 0.2 g of molybdenum trioxide, and the tert-butyl hydroperoxide/octane solution is gradually heated to reflux. The reaction mixture turns red as the temperature reaches 90° C. Low boiling materials are removed from the reaction mixture by fractional distillation. The reaction mixture is heated at reflux (110°-115° C.) for approximately one hour to discharge the red color. The mixture is cooled to 25° C. and stirred with 75 ml of 10% sodium thiosulfate solution for one hour to decompose unreacted hydroperoxide. The organic phase is dried over magnesium sulfate and concentrated to an oil. Purification by flash chromatography on silica gel (4:1 heptane: ethyl acetate) affords 10.6 g (88% yield) of the title compound, a yellow syrup.

Anal. Calcd. for $C_{35}H_{59}N_3O_6$: C, 68.0; H, 9.6; N, 6.8. Found: C, 68.1; H, 9.8; N, 6.9.

EXAMPLE 20 trans-(1-Octyloxy-2,2,6,6-tetramethylpiperidin-4-yl) alphacyanocinnamate

A mixture of 12.5 g (62.1 mmol) of trans-ethyl alphacyanocinnamate, 26.6 g (93.2 mmol) of 4-hydroxy-1-octyloxy-2,2,6,6-tetramethylpiperidine, and 100 ml of xylene is heated at reflux. Water is removed by fractional distillation. The reaction mixture is cooled to 80° C., treated with 0.3 g of lithium amide, and diluted with 50 ml of xylene. The mixture is heated at reflux for 2 hours while ethanol is removed by fractional distillation. The reaction mixture is diluted with diethyl ether (250 ml). The organic solution is washed with 1N hydrochloric acid (100 ml), saturated sodium bicarbonate solution (100 ml), and saturated sodium chloride solution (200 ml), then dried over magnesium sulfate and concentrated to a brown oil. Purification by flash chromatography affords 13.2 g (48% yield) of the title compound, a yellow, waxy solid.

Anal. Calcd. for $C_{27}H_{40}N_2O_3$: C, 73.6; H, 9.1; N, 6.4 Found: C, 73.7; H, 9.3; N, 6.2.

EXAMPLE 21

Ethyl 1-Cyclohexyloxy-2,2,6,6-tetramethylpiperidin-4-yl Benzalmalonate

A mixture of 15.0 g (60.4 mmol) of diethyl benzalmalonate, 32.4 g (127 mmol) of 1-cyclohexyloxy-4-hydroxy-2,2,6,6-tetramethylpiperidine, and 150 ml of toluene is heated at reflux. Water is removed by fractional distillation. The reaction mixture is cooled to 80° C. and treated with 1.0 g of titanium tetrabutoxide. The mixture is heated at reflux for 7 hours while ethanol is removed by fractional distillation. The reaction mixture is diluted with ethyl acetate (400 ml). The organic solution is washed with 1N hydrochloric acid (200 ml) and saturated sodium bicarbonate solution (200 ml), dried over magnesium sulfate, and concentrated to an oil. Purification by flash chromatography on silica gel (19:1 heptane: ethyl acetate) affords 27.6 g (54% yield) of the title compound, a colorless syrup, which is a mixture of geometric isomers.

Anal. Calcd. for $C_{27}H_{39}NO_5$: C, 70.9; H, 8.6; N, 3.1. Found: C, 70.7; H, 9.0; N, 2.9.

EXAMPLE 22

Bis(1-cyclohexyloxy-2,2,6,6-tetramethylpiperidin-4-yl) Benzalmalonate

The title compound, a white glass, is prepared in 90% yield according to the procedure in Example 21 by removing more distillate from the reaction mixture in order to increase the reaction temperature. The final temperature is 140° C., and the reaction time is 11 hours.

Anal Calcd for $C_{40}H_{62}N_2O_6$: C, 72.0; H, 9.4; N, 4.2. Found: C, 72.0: H. 9.4: N, 4.0.

EXAMPLE 23

2,4-Bis(2,4-dimethylphenyl)-6-{2-hydroxy-4-[(1-cyclohexyloxy -2,2,6,6-tetramethylpiperidin-4-yloxy)carbonylmethoxy]phenyl}-s-triazine The title compound, a yellow solid with mp 105°-109° C., is prepared in 54% yield from 1-cyclohexyloxy-2,2,6,6-tetramethylpiperidin-4-yl chloroacetate and 2,4-bis(2,4-dimethylphenyl)-6-(2,4-dihydroxyphenyl)-s-triazine according to the procedure of Example 8B.

Anal. Calcd. for $C_{42}H_{52}N_4O_5$: C, 72.8; H, 7.6; N, 8.1. Found: C, 72.2, H, 7.6; N, 7.9.

EXAMPLE 24

2,2'-Bis[N-(1-cyclohexyloxy-2,2,6,6-tetramethylpiperidin-4-yl) aminocarbonylmethoxy]oxanilide A solution of 15.0 g (45.3 mmol) of N-(2-cyclohexyloxy-2,2,6,6-tetramethylpiperidin-4-yl)-2-chloroacetamide in 50 ml of N,N-dimethylformamide is added over a 10 minute interval to a mixture of 6.2 g (22.7 mmol) of 2,2'-dihydroxyoxanilide, 100 ml of N,N-dimethylformamide, and 3.6 g (45.3 mmol) of 50% aqueous sodium hydroxide. The reaction mixture is heated at 50° C. for 1.5 hours and at 85° C for 30 minutes, then cooled to 40° C. Solids are isolated by filtration and washed with N,N-dimethylformamide. The crude product is suspended in water and then filtered to afford 14.1 g (72% yield) of the title compound, a light yellow solid, mp 275°-76° C. (dec).

Anal. Calcd. for $C_{48}H_{72}N_6O_8$: C, 66.9; H, 8.4; N, 9.8. Found: C, 66.8; H, 8.6; N, 9.6.

EXAMPLE 25

2-Hydroxy-4-{3-[N-(1-cyclohexyloxy-2,2,6,6-tetramethylpiperidin -4-yl)-amino]-2-hydroxypropoxy}benzophenone A mixture of 4.0 g (14.8 mmol) of 2-hydroxy-4-(2,3-epoxypropoxy)benzophenone, 3.8 g (14.8 mmol) of 4-amino-1-cyclohexyloxy-2,2,6,6-tetramethylpiperidine, and 40 ml of ethanol is heated at reflux for 2 hours. Ethanol is evaporated, and the residue is purified by flash chromatography on silica gel (2:1 hexane: ethyl acetate, then 1:1 hexane: ethyl acetate) to afford 1.2 g of a yellow oil which crystallizes upon standing. Recrystallization from a mixture of heptane and dichloromethane affords 0.6 g (8% yield) of the title compound, a yellow solid, mp 118°-121° C.

Anal. Calcd. for $C_{31}H_{44}N_2O_5$: C, 71.0; H, 8.5; N, 5.3. Found: C, 70.8; H, 8.4; N, 5.0.

EXAMPLE 26

2-Hydroxy-4-{3-[N-butyl-N-(1-cyclohexyloxy-2,2,6,6-tetramethylpiperidin -4-yl)amino]-2-hydroxypropoxy}benzophenone A mixture of 4.0 g (14.8 g mmol) of 2-hydroxy-4-(2,3-epoxypropoxy)benzophenone, 6.9 g (22.2 mmol) of 4-butylamino-1-cyclohexyloxy-2,2,6,6-tetramethylpiperidine, and 40 ml of ethanol is heated at reflux for 4 hours. Ethanol is evaporated, and the residue is purified by flash chromatography on silica gel (4:1 heptane: ethyl acetate) to afford 7.9 g (92% yield) of the title compound, a yellow oil.

Anal. Calcd. for $C_{35}H_{52}N_2O_5$: C, 72.4; H, 9.0; N, 4.8. Found: C, 70.6; H, 9.0; N, 4.6.

EXAMPLE 27

2-Hydroxy-4-[3-(1-cyclohexyloxy-2,2,6,6-tetramethyl-piperidin-4-yloxy)-2-hydroxypropoxy]benzophenone A mixture of 5.0 g (18.5 mmol) of 2-hydroxy-4-(2,3-epoxypropoxy)benzophenone and 15.0 g (58.7 mmol) of 1-cyclohexyloxy-4-hydroxy-2,2,6,6-tetramethylpiperidine is heated to 80° and then treated with 0.5 g of phosphorous acid (99%). The reaction mixture is heated at 80°-90° C. for 6 hours, then cooled and dissolved in ethyl acetate (200 ml). The organic solution is washed with saturated sodium bicarbonate solution (100 ml), dried over magnesium sulfate, and evaporated to a yellow oil. Purification by flash chromatography on silica gel to obtain the least polar material formed in the reaction mixture affords approximately 200 mg of the title compound, a yellow glass.

Anal. Calcd. for $C_{31}H_{43}NO_6$: C, 70.8; H, 8.2; N, 2.7. Found: C, 70.2; H, 8.6; N, 2.9.

EXAMPLE 28

Light Stabilization of Polypropylene

This example illustrates the light stabilizing effectiveness of instant stabilizers.

Polypropylene powder (Himont Profax 6501) stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

Each of the instant compounds protect the polypropylene from the deleterious effects of actinic light far longer than the time required for polypropylene to exhibit failure in this test when no stabilizer is present.

EXAMPLE 29

Stabilization of High Solids Thermoset Acrylic Resin Enamel

A thermoset acrylic enamel based on a binder of 70% by weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include an effective stabilizing amount of the test hindered amine light stabilizer having also present therein a UV-absorbing moiety.

Commercially available epoxy primed $4'' \times 12''$ (10.16 cm $\times$ 30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV for 1500 hours. The 20° gloss values of the panels are determined before and after exposure.

The loss of gloss of the stabilized panels is considerably less than that of the unstabilized control panels.

What is claimed is:

1. A compound having one of the formulas I to VII

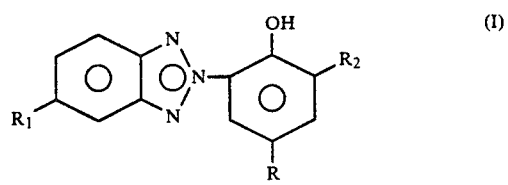

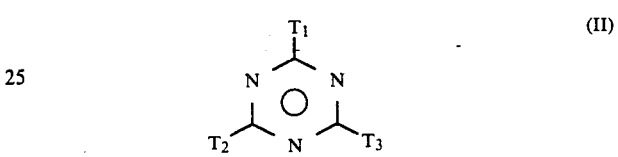

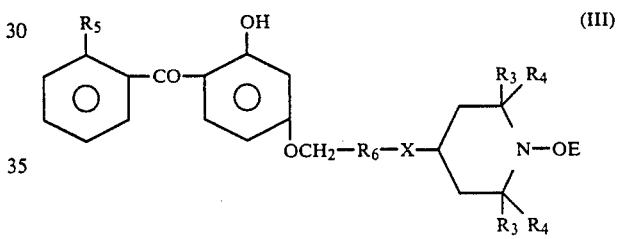

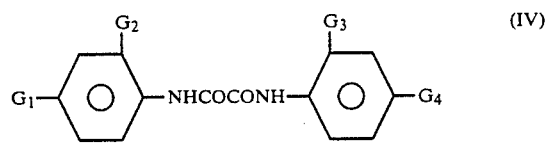

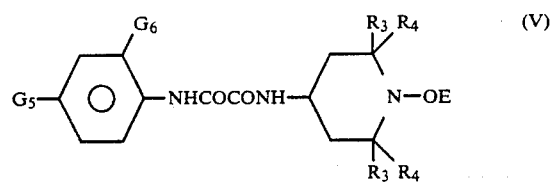

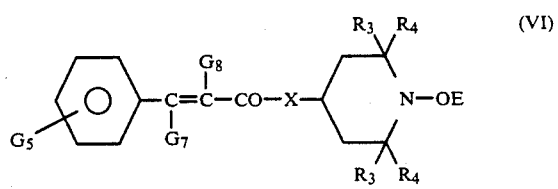

wherein $R_1$ is hydrogen, halogen, alkyl of 1 to 12 carbon atoms or aralkyl of 7 to 15 carbon atoms, R and $R_2$ are independently hydrogen, alkyl of 1 to 12 carbon atoms, aralkyl of 7 to 15 carbon atoms or the group of formula VII

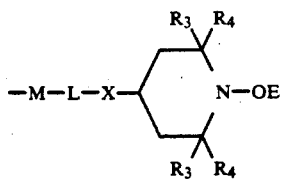

(VII)

with the proviso that one of $R_2$ and $R_3$ is a group of formula VII $R_3$ and $R_4$ are independently alkyl of 1 to 4 carbon atoms or together $R_3$ and $R_4$ are pentamethylene, M is a direct bond, $-NG_9-$, $-O-$, $-S-$, $-SO_2NG_9$, $-SO_2-$, $-SO_2O-$, $-CONG_9-$, $-COO-$ or $-OCO-$, L is a direct bond, alkylene of 1 to 12 carbon atoms, alkenylene of 3 to 18 carbon atoms, alkynylene of 3 to 18 carbon atoms, cycloalkylene of 5 to 12 carbon atoms, said alkylene interrupted by one or more $-O-$ atoms, X is $-COO-$, $-CONG_9-$, $-O-$, $-NG_9-$ or $-NY-$ where $G_9$ is hydrogen or alkyl of 1 to 8 carbon atoms, $R_5$ is hydrogen or hydroxyl, $R_6$ is $-CO-$, $-CHOHCH_2-$ or $-CH(CH_2OH)-$, $G_1$, $G_2$, $G_3$, and $G_4$ are independently hydrogen, halogen, alkyl of 1 to 12 carbon atoms, aryl of 6 to 10 carbon atoms, aralkyl of 7 to 15 carbon atoms, phenoxy, alkoxy of 1 to 12 carbon atoms, $-OCH_2COO-L_1$ or the group T where $L_1$ is alkyl of 1 to 8 carbon atoms, and T is

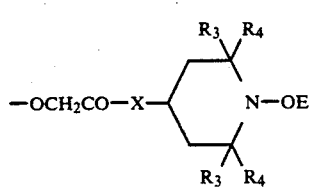

with the proviso that at least one of $G_1$ to $G_4$ must be T, $G_5$ and $G_6$ have independently the same definitions as $G_1$ to $G_4$, with the proviso that at least one of $G_5$ and $G_6$ do not need to be T, $G_7$ is hydrogen, phenyl or phenyl substituted by $G_5$, $G_8$ is cyano, $-COO-L$ or $-CO-X-Y$, where Y is 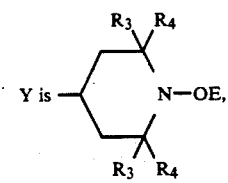

E is hydrogen, alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, $T_1$, $T_2$ $T_3$ are independently alkyl of 1 to 12 carbon atoms, aryl of 6 to 10 carbon atoms, said aryl substituted by one or two alkyl of 1 to 4 carbon atoms, aralkyl of 7 to 15 carbon atoms, $-OR_7$, $-SR_7$, $-NR_7R_8$, $-SO_3H$, or o-hydroxyphenyl substituted by the group T, with the proviso that at least one of $T_1$, $T_2$ and $T_3$ must be o-hydroxyphenyl substituted by the group T, and $R_7$ and $R_8$ are independently hydrogen, alkyl of 1 to 18 carbon atoms, alkenyl of 2 to 18 carbon atoms, alkoxyalkyl of 2 to 12 carbon atoms, cycloalkyl of 5 to 12 carbon atoms, aryl of 6 to 10 carbon atoms, said aryl substituted by one or two alkyl of 1 to 4 carbon atoms, aralkyl of 7 to 15 carbon atoms, or the group Y.

2. A compound according to claim 1 wherein $R_1$ is hydrogen, chloro, alkyl of 1 to 4 carbon atoms or alpha,alpha-dimethylbenzyl.

3. A compound according to claim 2 wherein $R_1$ is hydrogen or chloro.

4. A compound according to claim 1 wherein $R_2$ is alkyl of 1 to 8 carbon atoms or alpha,alpha-dimethylbenzyl.

5. A compound according to claim 4 wherein $R_2$ is methyl, tert-butyl, tert-amyl or tert-octyl.

6. A compound according to claim 1 wherein $R_3$ and $R_4$ are each methyl.

7. A compound according to claim 1 where $R_5$ is hydrogen.

8. A compound according to claim 1 where $R_6$ is $-CO-$.

9. A compound of formula IV according to claim 1 where $G_1$ and $G_4$ are each hydrogen.

10. A compound according to claim 1 where $G_5$ is hydrogen.

11. A compound according to claim 1 where $G_3$ or $G_6$ is T, ethoxy or $-OCH_2COO-L_1$ where $L_1$ is alkyl of 2 to 8 carbon atoms.

12. A compound according to claim 13 wherein $L_1$ is ethyl, n-butyl, n-octyl or isooctyl.

13. A compound according to claim 1 wherein $G_7$ is hydrogen.

14. A compound according to claim 1 wherein $G_8$ is cyano.

15. A compound according to claim 1 wherein X is $-O-$ or $-NH-$.

16. A compound according to claim 1 wherein E is alkyl of 1 to 12 carbon atoms, cyclohexyl or alpha-methylbenzyl.

17. A compound according to claim 18 wherein E is methyl, heptyl, octyl, nonyl, cyclohexyl or alpha-methylbenzyl.

18. A compound according to claim 1 wherein R is a group of formula VII where M is a direct bond, L is ethylene and X is $-COO-$.

19. The compound according to claim 1 which is 1-methoxy-2,2,6,6-tetramethylpiperidin-4-yl 3-(2H-benzotriazol-2-yl-5-tert-butyl-4-hydroxyhydrocinnamate.

20. The compound according to claim 1 which is 1-cyclohexyloxy-2,2,6,6-tetramethylpiperidin-4-yl 3(2H-benzotriazol-2-yl)-5-tert-butyl-4-hydroxyhydrocinnamate.

21. The compound according to claim 1 which is 1-octyloxy-2,2,6,6-tetramethylpiperidin-4-yl 3-(2H-benzotriazol-2-yl)-5-tert-butyl-4-hydroxyhydrocinnamate.

22. The compound according to claim 1 which is N-(1-octyloxy-2,2,6,6-tetramethylpiperidin-4-yl) -3-(2H-benzotriazol-2-yl)-5-tert-butyl-4-hydroxyhydrocinnamamide.

23. The compound according to claim 1 which is 2-hydroxy-4-[(1-octyloxy-2,2,6,6-tetramethylpiperidin-4-yloxy)-carbonylmethoxy]benzophenone; 2-hydroxy-4-[N-(1-methoxy-2,2,6,6-tetramethylpiperidin-4-yl) -N-butylaminocarbonylmethoxy]benzophenone; 2-hydroxy-4-[3-(N-(1-cyclohexyloxy-2,2,6,6-tetramethyl-piperidin-4-yl)amino) -2-hydroxypropoxy]benzophenone; 2-hydroxy-4-[3-(N-butyl-N-(1-cyclohexyloxy-2,2,6,6-tetramethylpiperidin-4-yl)amino) -2-hydroxy-propoxy]benzophenone; or 2-hydroxy-4-[3-(1-cyclohexyloxy-2,2,6,6-tetramethylpiperidin-4-yloxy) -2-hydroxypropoxy]benzophenone.

24. The compound according to claim 1 which is 2,4-bis(2,4-dimethylphenyl)-6-[2-hydroxy-4-((1-octyloxy -2,2,6,6-tetramethylpiperidin-4-yloxy)carbonylmethoxy) -phenyl]-s-triazine; or 2,4-bis(2,4-dimethylphenyl)-6-[2-hydroxy-4-((1-cyclohexyloxy-2,2,6,6-tetramethylpiperidin-4-yloxy)carbonylmethoxy)-phenyl]-s-triazine.

25. The compound according to claim 1 which is 2-ethoxy-2'-[N-(1-cyclohexyloxy-2,2,6,6-tetramethyl-piperidin-4-yl) aminocarbonylmethoxy]oxanilide; 2'-ethoxy-2-[(1-cyclohexyloxy-2,2,6,6-tetramethylpiperi-din-4-yloxy)carbonylmethoxy]oxanilide; 2,2'-bis[(1-cyclohexyloxy-2,2,6,6-tetramethylpiperidin-4-yloxy)-carbonylmethoxy]oxanilide; or 2,2'-bis[N-(1-cyclohex-yloxy-2,2,6,6-tetramethylpiperidin-4-yl) aminocar-bonylmethoxy]oxanilide.

26. The compound according to claim 1 which is N-(2-octyloxycarbonylmethoxyphenyl)-N'-(1-octyloxy-2,2,6,6-tetramethylpiperidin-4-yl)oxamide.

27. The compound according to claim 1 which is trans-(1-octyloxy-2,2,6,6-tetramethylpiperidin-4-yl) alpha-cyanocinnamate.

28. The compound according to claim 1 which is ethyl 1-cyclohexyloxy-2,2,6,6-tetramethylpiperidin-4-yl benzalmalonate; or bis(1-cyclohexyloxy-2,2,6,6-tet-ramethylpiperidin-4-yl) benzalmalonate.

29. A composition stabilized against the deleterious effects of actinic light which comprises
  (a) a polymer subject to the deleterious effects of actinic light, and
  (b) an effective stabilizing amount of a compound according to claim 1.

30. A composition according to claim 29 wherein the polymer is a polyolefin.

31. A composition according to claim 30 wherein the polyolefin is polypropylene.

32. A composition according to claim 29 wherein component (b) is 1-cyclohexyloxy-2,2,6,6-tetramethyl-piperdin-4-yl 3-(2H-benzotriazol-2-yl)-5-tert-butyl -4-hydroxyhydrocinnamate.

33. A composition according to claim 29 wherein the polymer is a coating system based on alkyd, acrylic, acrylic alkyd, polyester, epoxide, urethane, polyamide vinyl or epoxy-polyester resins.

34. A composition according to claim 33 which contains a UV absorber or additional light stabilizer.

35. A method for stabilizing an a synthetic polymer against oxidative, thermal or actinic degradation which comprises incorporating into said a synthetic polymer an effective stabilizing amount of a compound according to claim 1.

* * * * *